(12) United States Patent
Hess et al.

(10) Patent No.: US 6,489,562 B1
(45) Date of Patent: Dec. 3, 2002

(54) MEDICAL ELECTRICAL LEAD HAVING VARIABLE STIFFNESS TIP-RING SPACER

(75) Inventors: Douglas N. Hess, Maple Grove, MN (US); Peter B. McIntyre, Mounds View, MN (US); Richard D. Sandstrom, Scandia, MN (US); Michael A. Ruff, Blaine, MN (US)

(73) Assignee: Medtronic, INC, Minneapolis, MN (US)

( * ) Notice: Subject to any disclaimer, the term of this patent is extended or adjusted under 35 U.S.C. 154(b) by 0 days.

(21) Appl. No.: 08/831,373

(22) Filed: Apr. 1, 1997

(51) Int. Cl.⁷ .................................................. H01R 4/00
(52) U.S. Cl. ..................................... 174/84 R; 607/122
(58) Field of Search .................... 174/84 R, 152 GM; 607/119, 122, 127, 129

(56) References Cited

U.S. PATENT DOCUMENTS

| | | | |
|---|---|---|---|
| 3,902,501 A | 9/1975 | Citron et al. | 607/126 |
| 4,106,512 A | 8/1978 | Bisping | 607/127 |
| 4,217,913 A | 8/1980 | Dutcher | 607/127 |
| 4,951,687 A | 8/1990 | Ufford et al. | 607/122 |
| 4,967,766 A | 11/1990 | Bradshaw | 607/127 |
| 4,972,848 A | 11/1990 | DiDomenico et al. | 607/127 |
| 5,076,284 A | * 12/1991 | Hess et al. | 128/186 |
| 5,076,285 A | 12/1991 | Hess et al. | 607/127 |
| 5,228,455 A | 7/1993 | Barcel | 607/127 |
| 5,473,812 A | 12/1995 | Morris et al. | 29/825 |
| 5,514,172 A | * 5/1996 | Muellar | 607/122 |
| 5,643,694 A | * 7/1997 | Heller, Jr. | 174/152 GM X |

\* cited by examiner

*Primary Examiner*—Dean A. Reichard
*Assistant Examiner*—William H. Mayo, III
(74) *Attorney, Agent, or Firm*—Girma Wolde-Michael; Michael C. Soldner

(57) ABSTRACT

An implantable electrical lead having a tip electrode and a ring electrode located proximal to the tip electrode. A flexible spacer is located between the electrodes and includes a tubular plastic member having a thickness gradually increasing proximally and distally of a point intermediate the electrodes. Optionally the spacer includes an inner member of a lower durometer plastic, gradually decreasing in thickness proximally and distally from the intermediate point.

5 Claims, 4 Drawing Sheets

MEDICAL ELECTRICAL LEAD HAVING VARIABLE STIFFNESS TIP-RING SPACER

BACKGROUND OF THE INVENTION

The present invention is directed toward medical electrical leads generally, and more particularly toward cardiac pacing leads.

Endocardial pacing leads can generally be divided into two basic groups, depending upon the type of mechanism employed to maintain the electrode on the distal tip of the lead in contact with heart tissue. Leads employing mechanisms which do not penetrate heart tissue are typically referred to as "passive fixation" leads. Such leads are disclosed, for example, in U.S. Pat. No. 3,902,501 issued to Citron. Leads employing mechanisms which penetrate heart tissue are typically referred to as "active fixation" leads. The most common type of active fixation lead employs a helical fixation member which is screwed into heart tissue. Examples of such leads are disclosed in U.S. Pat. No. 4,106,512 issued to Bisping and U.S. Pat. No. 4,217,913, issued to Dutcher. These leads may include advancable fixation helixes, as in the Dutcher and Bisping patents previously cited, or may employ fixation helixes which are inextendable and mechanically coupled to the outer lead body, as disclosed in U.S. Pat. No. 5,076,285 issued to Hess et al and U.S. Pat. No. 5,473,812 issued to Morris et al. A hybrid between the two types may employ a lead with a fixation helix which is rotationally fixed with respect to the lead body, but which can be slid into and out of the distal end of the lead. Such leads are disclosed in U.S. Pat. No. 4,967,766 issued to Bradshaw, U.S. Pat. No. 5,228,455 issued to Barcell.

In both active and passive fixation leads, it is often desirable to employ electrodes in a bipolar configuration, such that located proximal to the tip electrode, is a second electrode, typically taking the form of a conductive ring encircling the lead body. The electrode assembly at the distal tip of the lead and the ring electrode, are typically quite rigid, with the lead body intermediate the tip and ring comprising a tip-ring spacer of some sort carrying a single conductor. Because the lead body proximal to the ring electrode carries two conductors, it is typically stiffer than the portion of the lead intermediate to tip and ring electrodes. The result of this basic structural arrangement is that bending forces applied to the distal portion of the lead, for example due to contraction of the heart, tend to localize bending in the tip-ring spacer region of the lead. With some present designs, bending tends to uneven along the length of the tip-ring spacer, with small radius bends occurring adjacent the proximal end of the tip electrode assembly and/or the distal end of the ring electrode, raising the possibility of stress induced conductor fractures at these points.

The present invention is directed toward providing a lead with an improved tip-ring spacer, optimized to provide a controlled radius of curvature throughout the length of the tip-ring spacer and to avoid areas of high radius of curvature which might otherwise occur. The tip-ring spacer of the present invention accomplishes this goal by means of an internal lumen having a dual-taper configuration. The spacer has a generally uniform outer diameter while the central lumen therethrough has an inner diameter which increases gradually from a first diameter at its proximal end to a second diameter at a point intermediate the proximal distal ends of the spacer, and which gradually tapers distally to a third, reduced diameter adjacent the proximal end of the electrode assembly. In one preferred embodiment of the invention, the tip-ring spacer is formed of a material having a relatively high modulus of elasticity, in order to resist bending stress at the proximal and distal ends of the spacer, and is provided with an insert having a lumen therethrough of a generally uniform diameter, and an outer configuration corresponding to the inner configuration of the lumen through the tip-ring spacer. This insert may be provided by molding or backfilling, and preferably has a lower modulus of elasticity, optimized to balance the overall bending characteristics of the lead in the tip-ring space region to provide for a uniform radius of curvature along the length of the tip-ring spacer. Alternatively, a lower modulus material may be chosen for the spacer, and the dual-tapered lumen may be left unfilled.

The present invention is particularly beneficial in leads employing helical fixation devices, as in such leads, the conductor coupled to the fixation helix is typically a high torque, coil conductor in which the individual coil wires typically have a cross section greater than that which might be employed in a passive fixation lead, which in turn may result in a reduced ability to withstand repeated flexing over a small radius of curvature. However, the invention is also believed to be useful in the context of passive fixation leads as well.

DETAILED DESCRIPTION OF THE PREFERRED EMBODIMENT

Figure 1:
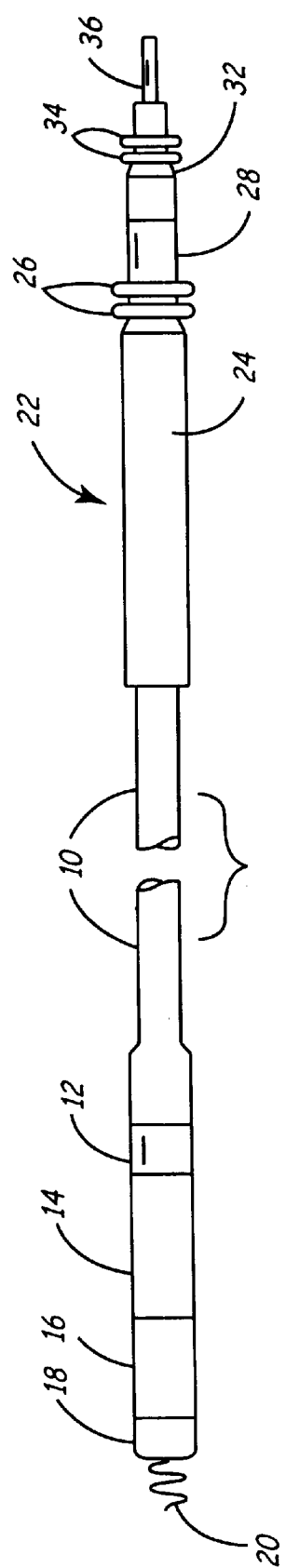
FIG. 1 is a plan view of an active fixation pacing lead employing the present invention.

FIG. 1 illustrates a planned view of an active fixation lead of the type employing a helix advancable from the distal end of the electrode which employs the present invention. The lead includes a lead body which has an outer insulative sheath 10 which may be formed of biocompatible plastics such as silicone rubber or polyurethane, commonly used in the context of cardiac pacing leads. At the distal end of the lead is an electrode head 16, provided with a distal cap 18, through which the fixation helix 20 emerges. Electrode head 16 may be manufactured of a relatively rigid plastic, such as a polyurethane and defines a housing into which the helix 20 may be retracted. Helix 20 is formed of a conductive biocompatible metal such as platinum-iridium alloy and serves as the distal, tip electrode for the lead. Proximal to helix 20 is a ring electrode 12, which may be fabricated of a biocompatible metal such as platinum-iridium alloy or stainless steel. Tip-ring 14 separates electrode head 16 from ring 12, and is described in more detail in FIG. 2 below.

At the proximal end of the lead is a connector assembly 22 which includes an elongated connector sleeve 24 which carries two sealing rings 26. Proximal to sealing rings 26 is a connector ring 28 which is coupled to a coiled conductor within the lead body, which extends and is coupled to ring electrode 12. A second sleeve 32 is provided with additional sealing rings 34 to provide a fluid seal intermediate connector pin 36 and connector ring 28. Connector pin 36 is rotatably mounted within the connector assembly, in the manner disclosed in U.S. Pat. No. 4,951,687, incorporated herein by reference in its entirety. Connector pin 36 is coupled to a coil conductor which extends distally within the lead body to the helix 20. Rotation of connector pin 36 and the coiled conductor attached thereto causes helix 20 to be screwed out of or retracted into electrode head 16, depending upon the direction of rotation. Connector ring 28 and connector pin 32 may be fabricated of a biocompatible conductive metal, such as stainless steel. Sleeves 24 and 32 may be fabricated of a biocompatiblle, resilient polymer such as silicone rubber. The external configuration of connector assembly 22 corresponds to the "IS-1" international connector standard.

Figure 2:
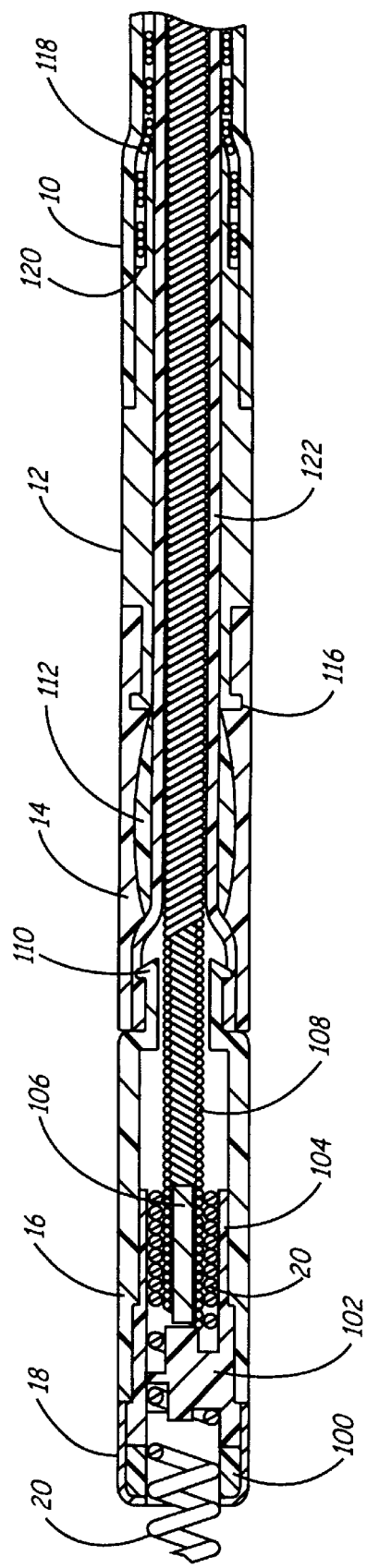
FIG. 2 is a sectional view of the lead through FIG. 1 in the area of the tip-ring spacer.

FIG. 2 is a sectional view through the distal portion of the lead illustrated in FIG. 1. In this view, it can be seen that helix 20 is coupled to an elongated coil conductor 108 (in turn coupled to connector pin 36) by means of a crimping core 106 located within conductor 108 and a crimp sleeve 104, located external to the proximal portion of helix 20. The close-wound proximal portion of helix 20 and conductor 108 are compressed between crimp sleeve 104 and crimp core 106 to provide electrical and mechanical interconnection. Rotation of conductor 108 causes helix 20 to be screwed into and out of electrode head 16 by means of engagement with the coil guide member 102, which defines a helical path along which coil 20 is advanced or retracted. Cap 18 serves to retain a monolithic controlled release device 100 in place, around helix 20, as described in U.S. Pat. No. 4,972,848 issued to DiDominico et al., also incorporated herein by reference in its entirety.

The proximal end of electrode head 16 is provided with shoulders 110, which serve to engage and retain the tip-ring spacer 14 and the inner lead insulation 122, which surrounds coil conductor 108. Inner insulation 122 is typically fabricated of silicone rubber, however, in some embodiments polyurethane may be substituted. Tip-ring spacer 14 may be fabricated of polyurethane, and compresses the distal end of inner insulative sheath 122 against the shoulders 110 located at the proximal end of the electrode head 16. The distal end of the ring electrode 12 is similarly provided with shoulders 116 which engage in a corresponding circumferential groove molded into tip-ring spacer 14, retaining these two elements in engagement with one another. Between the shoulder 116 on ring electrode 12 and the proximal end of electrode head 16, tip-ring spacer 14 defines an internal lumen having a diameter which gradually increases from a first diameter at a first point adjacent shoulder 116 to a second, larger diameter at a second point intermediate electrode head 16 and ring electrode 12, and thereafter decreases gradually to a third, smaller diameter at a third point adjacent the proximal end of electrode head 16. The wall thickness of the spacer correspondingly decreases gradually from the first point to the second point and gradually increases from the second point to the third point. An inserted or backfilled tubular member 112, which is preferably fabricated out of a lower durometer material such as silicone rubber, is also visible in cross section, where it can be seen that it gradually increases in wall thickness from the first point to the second point and then gradually decreases in wall thickness from the second point to the third point, such that the composite structure of spacer 14 and member 112 defines a tubular member of generally uniform wall thickness but varying flexibility. The configuration of tip-ring spacer 14 in conjunction with the inserted or backfilled member 112 provides a structure in which bending forces are distributed along the length of the tip-ring spacer 14, providing for a smooth bend having a single, gradual radius of curvature, as opposed to an abrupt bend of small radius of curvature adjacent either the distal end and of the ring electrode 12 or the proximal end of the electrode head 16.

Also visible in this view are the outer conductor 118 which is coupled to a reduced diameter portion of the ring electrode, and welded to the ring electrode adjacent to the shoulder 120. Outer insulative sheath 10 is visible enclosing the proximal portion of the ring electrode 112 and outer conductor 118. Outer conductor 118 is coupled to the connector ring 28 at the proximal end of the lead. Inner conductor 108 and outer conductor 118 are fabricated of biocompatible metals such as MP35N stainless steel, Elgiloy, drawn brazed strand (DBS) wire or other known conductor materials for use in implantable leads.

Figure 3:
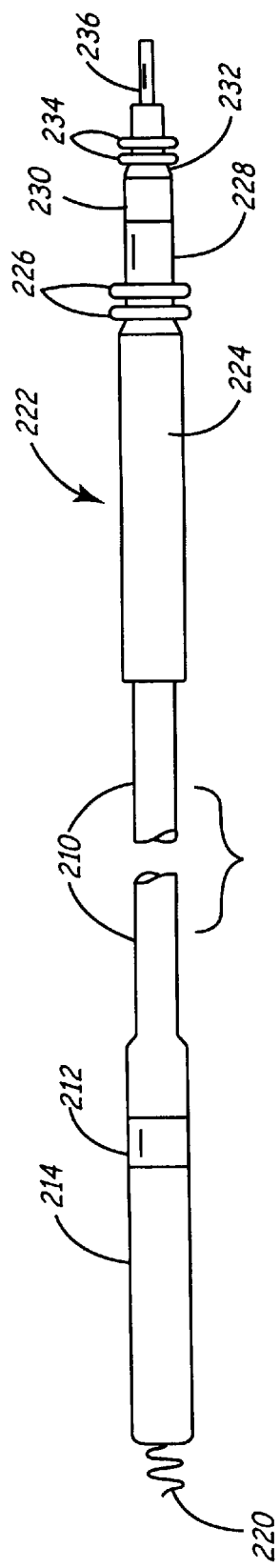
FIG. 3 is a plan view of a second, active fixation lead practicing the present invention.

FIG. 3 is a plan view of an alternative embodiment of a lead employing the present invention. This lead is provided with a fixation helix 220 which is fixedly mounted in the lead body, so that in order to screw the helix 220 into heart tissue, the entire lead body must be rotated. In this embodiment, rather than employing a rigid electrode head, the lead is provided with an elongated tip-ring spacer 214 which extends from the distal end of the lead proximally to ring electrode 212. Outer insulative sleeve 210 extends proximally from ring electrode 212 to connector assembly 222. Connector assembly 222 is provided with a connector sleeve 224, which carries sealing rings 226. Connector ring 228 is coupled to ring electrode 212, and is separated from connector pin 236 by a molded spacer 230, around which a second sleeve 232, provided with sealing rings 234 is mounted. As in FIG. 1, sleeves 222 and 232 may be fabricated of silicone rubber. Connector ring 228 and connector pin 236 may be fabricated of stainless steel, and spacer 230 may be fabricated of a rigid plastic such as a polyurethane.

Figure 4:
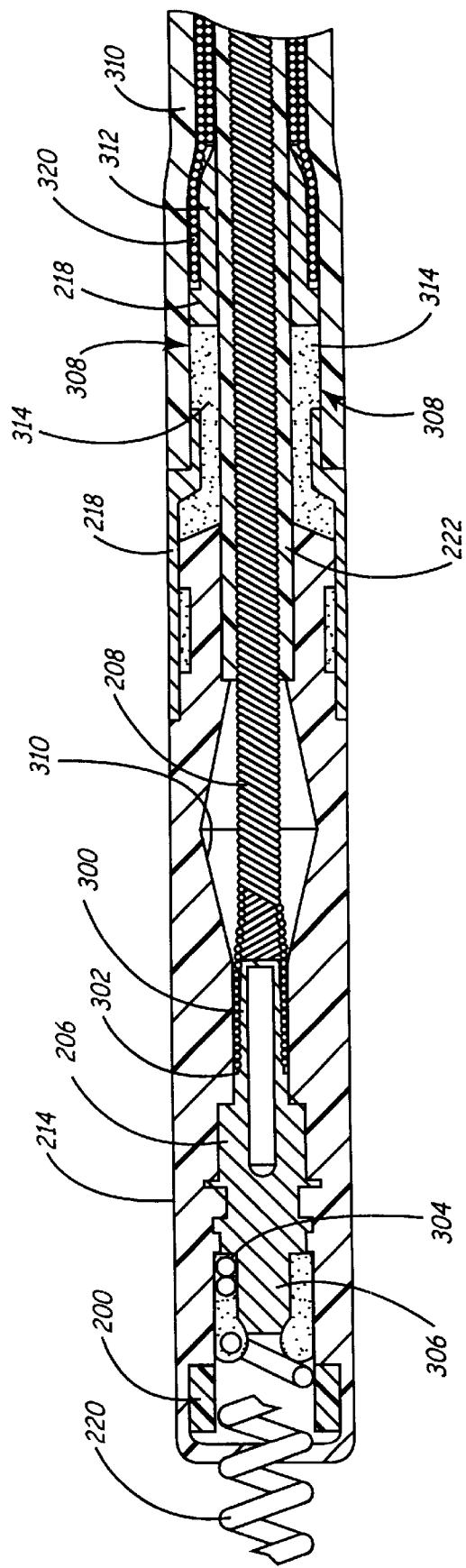
FIG. 4 is a sectional view through the lead of FIG. 3, illustrating the area of the tip-ring spacer.

FIG. 4 is a sectional view through the distal portion of the lead of FIG. 3. The inner conductor coil 208 is coupled to the helix 220 by means of a welding core 206. The proximal portion of helix 220 is slid over cylindrical portion 306 of core 206, and is welded against shoulder 304. Similarly, inner conductor 208 is slid over a second cylindrical portion 300 of the core as welded against shoulder 302. Mounted within tip-ring spacer 14 is a monolithic controlled release device 200, corresponding to the monolithic controlled release device 100, illustrated in FIG. 2.

Like the tip-ring spacer 14 of the lead illustrated in FIGS. 1 and 2, tip-ring spacer 214 is provided with an internal lumen 311 which increases in diameter from a first diameter adjacent the distal end of the electrode ring 212, expands to a larger inner diameter and then gradually decreases to a smaller inner diameter adjacent the proximal end of the welding core 206. In this embodiment of the invention, however, the tip-ring spacer 214 is not provided with a backfill or an insert, and is manufactured of a lower durometer material than spacer 14 (FIG. 2), such as silicone rubber.

Ring electrode 218 is mounted surrounding the proximal end of tip-ring spacer 214, and defines a reduced diameter, cylindrical portion 312, around which the outer conductor coil 219 is mounted, welded against shoulder 320. In the portion of the ring electrode between the exposed section of the electrode and cylindrical portion 312, there are provided two apertures 308, allowing backfill of silicone rubber 314 to bond outer insulative sleeve 210, inner insulative sleeve 222 and the ring electrode 218 together.

The embodiments illustrated above both take the form of leads employing active fixation electrodes, which often employ high torque coiled conductors, which by virtue of their increased thickness, may provide a reduced resistance to fracture in response to repetitive bending around small radius of curvature. The present invention is thus, particularly beneficial in the context of these types of leads. However, it should be understood that the invention is as well believed to be beneficial in conjunction with leads employing passive fixation mechanisms such as tines, flanges or fins, or leads employing other forms of active fixation. Similarly, the leads above both take the form of leads in which the tip-ring spacer separates a tip electrode from a conductive, ring electrode. However, the basic mechanism for controlling the distribution of bending stress provided by the present invention is believed as useful in leads in which one or more of the electrodes is substituted by a sensor, such as an oxygen sensor or pressure sensor, which structurally will have a rigid housing not dissimilar to a ring electrode, in the context of the present invention. Use of the optimized tip-ring spacer according to the present invention to separate sensors from one another or to separate electrodes from sensors is thus also believed within the scope of the present invention. Finally, in both disclosed embodiments the fixation helix serves as the tip electrode. However, the invention is also valuable in the context of leads in which the conductor is not coupled to the helix, and a separate electrode is provided, as in the above-cited Dutcher patent As such, the present invention should be considered as exemplary, rather than limiting, with regard to the claims that follow.

What is claimed is:

1. A medical electrical lead comprising:

an elongated insulative lead body;

a distal electrode located adjacent a distal end of the lead body;

a proximal electrode located on said lead body proximal to and spaced from the distal electrode;

first and second electrical connectors located adjacent a proximal end of the lead body;

first and second conductors extending from the first and second connectors to the proximal and distal electrodes, respectively; and a flexible spacer located between the proximal and distal electrodes, having an outer surface and central lumen and having a wall thickness separating the outer surface and an interior surface of the lumen which gradually decreases from a first point adjacent the proximal electrode to a second point intermediate the proximal and distal electrodes and gradually increases from the second point to a third point adjacent the distal electrode.

2. A medical electrical lead comprising:

an elongated insulative lead body;

a first rigid lead component located on the lead body;

a second rigid lead component located proximal to and spaced from the first rigid component, on the lead body an electrical connector located adjacent a proximal end of the lead body;

a conductor extending from the connector to the first rigid lead component; and a flexible spacer located between the first and second rigid lead components, having an outer surface and central lumen and having a wall thickness separating the outer surface and an interior surface of the lumen which gradually decreases from a first point adjacent the second rigid component to a second point intermediate the first and second rigid components and gradually increases from the second point to a third point adjacent the first rigid component.

3. A lead according to claim 2 wherein said first and second rigid components are electrodes.

4. A lead according to claim 1 or claim 2 or claim 3 wherein the spacer is fabricated of a plastic having a first durometer and wherein the lead further comprises a tubular member located within the spacer and fabricated of a plastic having a second, lesser durometer and having a thickness increasing from the first point to the second point and decreasing from the second point to the third point.

5. A lead according to claim 4 wherein the tubular member is located within the lumen of the spacer.

* * * * *